United States Patent
Liljenberg et al.

(10) Patent No.: US 6,935,164 B2
(45) Date of Patent: Aug. 30, 2005

(54) REFINER CONTROL

(75) Inventors: Thomas Liljenberg, Västerås (SE); Stefan Backa, Karlstad (SE); Lennart Thegel, Västerås (SE)

(73) Assignee: ABB AB, Västeraås (SE)

(*) Notice: Subject to any disclaimer, the term of this patent is extended or adjusted under 35 U.S.C. 154(b) by 0 days.

(21) Appl. No.: 10/332,954
(22) PCT Filed: Jun. 27, 2001
(86) PCT No.: PCT/SE01/01466
§ 371 (c)(1), (2), (4) Date: Jun. 17, 2003
(87) PCT Pub. No.: WO02/06815
PCT Pub. Date: Jan. 24, 2002

(65) Prior Publication Data
US 2004/0022128 A1 Feb. 5, 2004

(30) Foreign Application Priority Data
Jul. 14, 2000 (SE) .............................. 0002668

(51) Int. Cl.$^7$ .................. G01N 33/34; G01N 33/46; G01N 29/00; G01S 15/00
(52) U.S. Cl. ............... 73/53.03; 73/54.41; 73/61.75; 367/95; 367/96
(58) Field of Search ............... 73/53.03, 54.41, 73/61.71, 64.53; 367/95, 96

(56) References Cited

U.S. PATENT DOCUMENTS

| | | | |
|---|---|---|---|
| 3,710,615 A | | 1/1973 | Johnson et al. |
| 3,914,984 A | | 10/1975 | Wade |
| 4,574,624 A | * | 3/1986 | Lehtinen et al. ........... 73/54.04 |
| 5,714,691 A | | 2/1998 | Hill |
| 6,029,507 A | | 2/2000 | Faber et al. |
| 6,370,448 B1 | * | 4/2002 | Eryurek ........................ 700/282 |
| 6,523,395 B1 | * | 2/2003 | Kahkonen ................... 73/53.04 |

FOREIGN PATENT DOCUMENTS

| | | | | |
|---|---|---|---|---|
| FR | 2772476 | | 6/1999 | |
| WO | WO 91/10904 | * | 7/1991 | .................. 73/587 |
| WO | 99/15890 | | 4/1999 | |
| WO | 00/00793 | | 1/2000 | |

OTHER PUBLICATIONS

H. Martens et al., Multivariate Calibration, pp. 116–163, 1989.

M. Karras et al., Pulp Suspension Flow Measurement Using Ultrasonics and Correlation, 1982 Ultrasonics Symposium, 1982 IEEE, pp. 915–918.

D.J. Adams, PhD. MSc., Ultrasonic Propagation in Paper. Fibre Suspensions, pp. 187–194, *3rd International IFAC Conference On Instrumentation And Automation In The Paper, Rubber and Plastics*, May 1976.

J. Sundholm, Papermaking Science and Technology, Book 5, Mechanical Pulping, 1999, pp. 125–138.

* cited by examiner

*Primary Examiner*—Michael Cygan
(74) *Attorney, Agent, or Firm*—Venable LLP; Eric J. Franklin

(57) ABSTRACT

In the present invention a refiner (108) of a mechanical pulping line is supplied with a controllable acoustic source (14), arranged for emitting acoustic signals into the pulp fluid. The controllable acoustic signal is allowed to interact with the fibres in the pulp, and the acoustic (pressure) signals resulting from such an interaction is measured. At least one spectral component is measured. The measured spectral component is used to predict properties, content and/or size of the fibres. These properties may then be used to control the refiner (108) process. The used acoustic signal has preferably a wavelength that is large compared with a typical site of the particles.

33 Claims, 10 Drawing Sheets

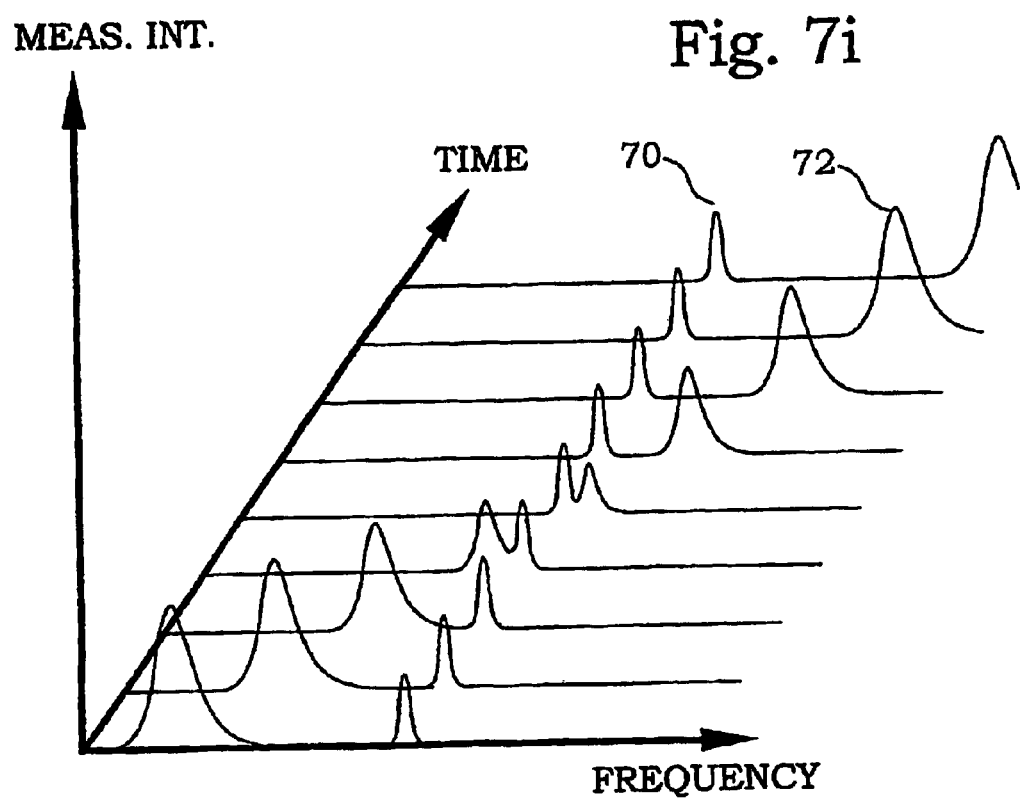

REFINER CONTROL

This application is a national stage entry of PCT/SE01/01466, filed 27 Jun. 2001.

TECHNICAL FIELD

The present invention generally relates to devices and methods used for paper manufacturing, and in particular to devices and methods concerning refining of pulp in a mechanical pulping process.

BACKGROUND

The quality of the paper resulting from a paper manufacturing process depends on many parameters associated with the pulp. In the pulp making industry there is a general shortage of reliable measurement techniques for characterisation of the pulp. Futhermore, true on-line techniques are even more rare. Thus, the control and quality assessment of the processes can not be accomplished in an efficient manner.

The refining process step in a mechanical pulping process is one of the most important steps of the entire paper making process. The way to operate the refining determines many of the most important properties of the resulting pulp. It is therefore desirable to be able to control the result from the refining process very carefully, in order to adjust the operation of the refining.

Some basic types of measurement philosophies exist for measuring pulp properties; "off-line", "on-line", "at-line" and "in-line".

The classical off-line procedure is to extract samples of the pulp for analysis in a laboratory. However, in this way only a part of the pulp is analysed, and the possible feedback of such an analysis is generally slow. An analysis method suitable for providing data for control purposes has to be performed in direct contact with the actual pulp flow.

To speed up the off-line procedure (up to 5–10 times) an on-line procedure with automatic sampling systems have been developed in which measurements based on e.g. optical measurement techniques are used. Typically such systems operate by diverting a small portion of the pulp into a special pipe or volume. One example being the PQM system (Pulp Quality Monitor) from Sunds Defibrator, which measures freeness, fibre length and shive content in a pulp suspension.

A common problem with all off-line and some on-line and at-line methods is that only a part of the flow is measured. The properties in such a diversion flow may differ from the main flow. TCA (Thermomechanical pulp Consistency Analyser) from ABB AB measures the consistency of the pulp. The system is using fibre optic techniques. Other similar systems are the Smart Pulp Platform (SPFM) available from ABB AB, and "Fiber Master" developed by the Swedish pulp and paper research institute (SITFI).

In-line methods, which operates directly on the entire pulp without extracting fluid into a special test space, are generally faster than off-line methods and can reduce some of the problems listed for these methods. However, mechanical devices have to be inserted in the process line in order to extract the flow sample, which may disturb the main flow and which makes maintenance or replacement work difficult. Furthermore sensors may be contaminated, or the flow may be contaminated by the sensors.

An alternative to use optical or electromagnetic waves is to use mechanical (acoustical) waves. This has several advantages. Acoustic waves are enviromentally friendly and also unlike electromagnetic waves they can propagate in all types of fluids.

In the article "Ultrasonic propagation in paper fibre suspensions" by D. J. Adams, 3rd International IFAC Conference on Instrumentation and Automation in the Paper, Rubber and Plastics Industries, p. 187–194, Noordnederlands Boekbedrijf, Antwerp, Belgium, it is disclosed to send ultrasonic beams of frequencies between 0.6 MHz and 15 MHz through a suspension of fibres and the attenuation as well as the phase velocity can be measured as a function of frequency. It is by this possible to obtain information about fibre concentration, size and to some extent the fibre state. However, an elaborate calibration procedure is necessary in order to make the method operable.

In "Pulp suspension flow measurement using ultrasonics and correlation" by M. Karras, E. Harkonen, J. Tomberg and O. Hirsimald, 1982 Ultrasonics Symposium Proceedings, p. 915–918, vol. 2, Ed: B. R. MCAvoy, IEEE, New York, N.Y., USA, a transit time measurement system is disclosed. The system measures primarily the mean flow velocity and tests from various pulp suspensions are described. Doppler shift measurements are used to determine velocity profiles. A frequency of 2.5 MHz was used.

In the international patent application WO99/15890, a method and a device for pulp process monitoring using acoustic measurements were disclosed. Inherent acoustical fields in the system (up to 100 kHz) are recorded indirectly via wall vibration measurements on a conveyor line, through which a pulp suspension flows. The recordings are graded by a data manipulation program according to predetermined characteristics and a vibration characteristics is generated. Stored vibration characteristics related to earlier recordings are compared at each recording for correlation to the properties of the suspension. The recorded vibrations can be used for controlling the process in a suitable way, for raising alarms at fault situations or for showing changed tendencies.

Since the method used in the above patent is based on a method which makes use of inherently appearing vibrations a number of problems result. One being that not only will sound generated in the fluid be picked up but also vibrations from mechanical sources, e.g., pumps, connected to the fluid. This leads to large amounts of disturbances, which increases the amount of averaging or overdetermination. Futhermore, since there are no control of the source, process methods for suppressing disturbances are difficult to apply. In addition the suggested method must be calibrated for each individual site, since the inherent vibrations are site dependent. This last aspect is a considerable practical limitation since it will cause very large losses in production upon installation.

SUMMARY

A general object of the present invention is to improve the control of a pulp refining process in order to achieve desired pulp properties. One object of the present invention is therefore to provide a pulp analysis method which is fast and reliable enough for real-time process control purposes. A further object is to improve the ratio "signal-noise" or "signal-disturbances" in pulp property measurements. Yet another object with the present invention is to make the data treatment of measurement more efficient.

The above objects are achieved by methods and apparatuses according to the enclosed claims. In general words, a controllable acoustic source is arranged in contact with the pulp flow in connection with a refiner. The controllable acoustic source emits a signal into the pulp. The controllable acoustic signal is allowed to interact with the fibres, and at least one spectral component of the acoustic signals (pressure, wall vibrations) resulting from such an interaction is measured via a sensor. At least one spectral component of the acoustic signals is measured. The measured spectral component(s) is (are) correlated to chemical/physical properties, content, distribution and/or size of the pulp fibres and are further used to control a refining process. The measured spectral component has preferably a wave length that is large compared to the typical size of the pulp fibres and distance between the pulp fibres. The used acoustic signal is thus typically of a frequency below 20 kHz.

Since the emitted acoustic signal is controllable, preferably by amplitude, frequency, phase and/or time-delay, the controllable acoustic signal can be selected to emphasise acoustic behaviours of the fibres in the pulp, e.g. by tuning the frequency to characteristic frequencies of the fibres. Furthermore, the signal can comprise one or several single frequencies or frequency bands, which also may vary with time. The controllable acoustic signal may also be emitted during limited time intervals or being amplitude modulated, which enables different noise and disturbance removal procedures on the measured acoustic signals in order to increase the signal/noise ratio.

By measuring not only frequency and corresponding amplitude of the resulting acoustic signal, but also phase, time or spatial dependencies, statistical modelling based on, e.g., multivariate analysis or neural networks may be utilised to make the analysis further robust. The spatial dependence is realised by using special geometric arrangements of sensors along and/or perpendicular to the flow direction.

The information from the measured acoustic signals is ether used, for controlling a refiner processes in a pulping system. The measurements may be performed upstream of the refiner in order to characterise the wood entering the refiner, i.e. feed-forward information, and/or downstream of the refiner in order to provide feedback information about the result of the refining process.

The advantages with the present invention is that it provides a monitoring and/or controlling method which is non-destructive, environmentally friendly and provides, depending on the averaging necessary, data in "realtime". The controllability of the acoustic source and the possibility to tune the frequency to a specific range makes it possible to emphasise important spectral characteristics of the pulp and allows for noise and disturbance reduction. Furthermore, with a controllable acoustic source, different acoustic propagation paths can be excited and used for analysis purposes. The present invention also provides the opportunity for multi-component analysis. No sample treatment is involved and the new method has the potential of being possible to use within a large concentration range and also at high temperatures. Finally, laboratory tests have demonstrated the feasibility of the method to perform "real-time" measurements of size and stiffness for cellulose fibres.

Further advantages and features are understood from the following detailed description of a number of embodiments.

BRIEF DESCRIPTION OF THE DRAWINGS

The invention, together with further objects and advantages thereof, may best be understood by making reference to the following description taken together with the accompanying drawings, in which:

FIGS. 7a–7i are diagrams illustrating examples of emitted acoustic signals or measured acoustic signals in different simplified situations.

DETAILED DESCRIPTION

Figure 1A:
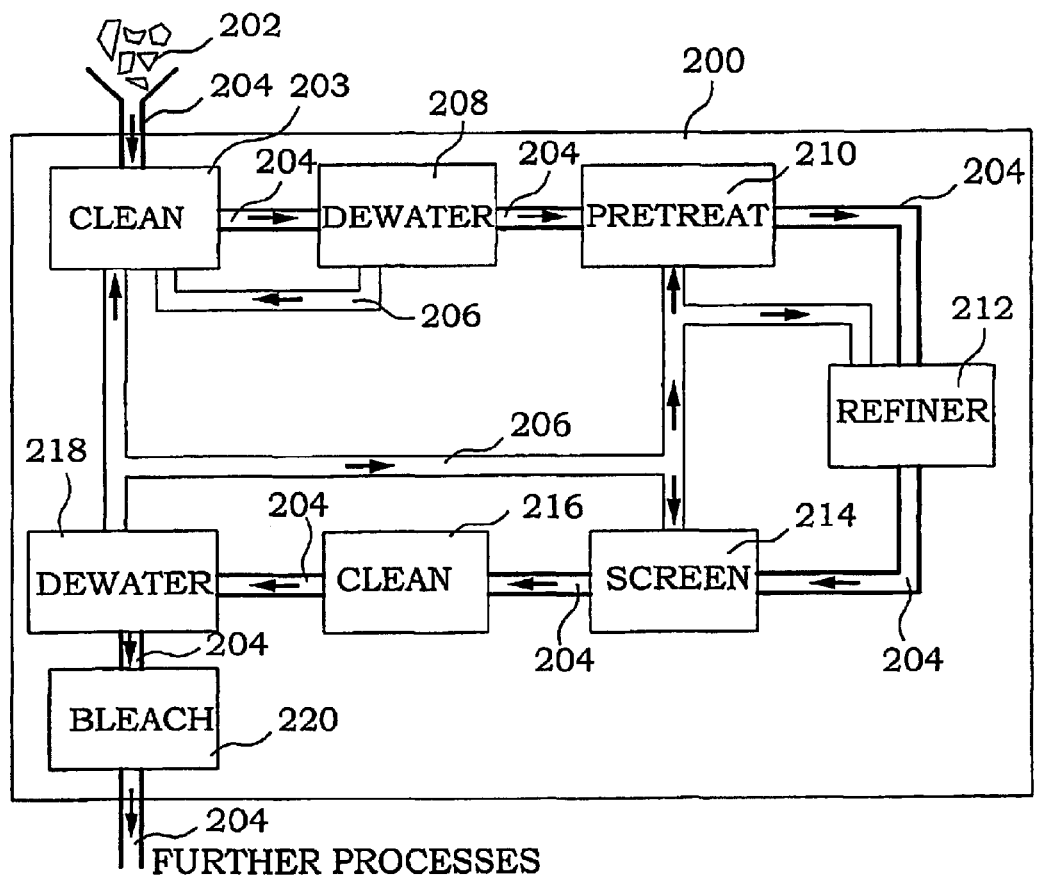
FIG. 1a is a schematic drawing of a typical mechanical pulping equipment.

FIG. 1a schematically illustrates a typical mechanical pulping process line 200 as a block scheme. Wood chips 202 are entered into the process line 200 into a cleaning unit 203, where the wood chips are cleaned from contaminants, e.g. particles of dirt and grit, by use of e.g. centrifugal cleaners or rotating screens. The cleaned wood chips are forwarded through a process pipe 204 into a dewatering unit 208. All pipes transporting chips or pulp are drawn with thick lines and some of them are denoted by 204. In the dewatering unit 208, the excess amount of water is removed. However, a certain amount of water is used to give the chips a suitable moisture. A part of the removed water is fed back to the cleaning unit for reuse, by a water reuse pipe 206. All water reuse pipes are drawn by thin lines, and the flow direction is indicated by arrows.

The dewatered and moistured wood chip is fed to a pretreatment unit 210, where e.g. a chemical impregnation or similar processes can be preformed, together with a preheating with pressurised steam. The pre-treated wood chips are then fed under pressure into a refiner 212 mixed with additional water. In the refiner, the wood chips are ground into pulp. The fibres must be mechanically beaten before the fibres become suitable for papermaking. In mechanical pulping processes this takes place during the refining step. The refining process separates the fibres from each other and also loosens-up the fibre structure, since the fibres otherwise will be too stiff for a high quality paper. The fibres are separated and fatigued by vibrational forces caused by the refiner 212.

In an ideal mechanical pulping process, the fibres must of course be separated from the wood, but the fibre length should be retained as far as possible. Futhermore, the fibres has to be delaminated, e.g internal fibrillation of the fibre wall. Abundant fines have to be removed from the middle lamella and the primary and secondary layers of the fibre wall. Also, the remaining secondary wall should be fibrillated, so called external fibrillation.

Normally, one distinguishes between different types of pulp, depending on the actual process. RMP (Refiner Mechanical Pulp) is referred to as an atmospheric refining of chips using a disc refiner. PRMP (Pressure Refiner Mechanical Pulp) is similar to RMP, but refining is performed pressurized and at an elevated temperature. In TMP (thermomechanical Pulp), the chips are preheated with steam and refined under pressure at elevated temperature. The refiner 212 of FIG. 1a is intended to be a TMP refiner.

The grounded pulp is depressurised and fed into a screening unit 214, where a further dilution with water and removal of fine particles is performed. The pulp is then entered into a vortex cleaner 216 where further contaminating particles are removed. The resulting pulp is then dewatered in a dewatering unit 218. The removed water is reused in earlier steps, e.g. in the cleaning unit 203, the pretreatment unit 210, the refiner 212 or the screening unit 214, by water reuse pipes. The pulp is eventually bleached in a bleacher unit 220 and is then transported to further processing in a paper manufacturing line or to a pulp storage.

Figure 1B:
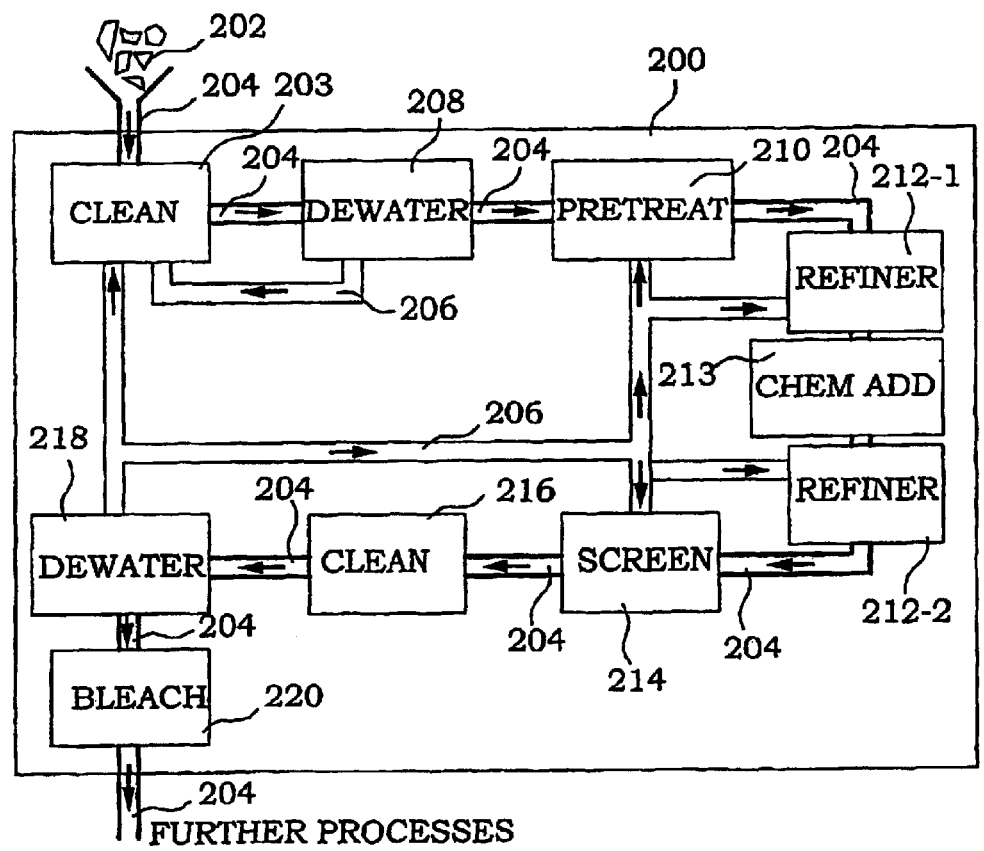
FIG. 1b is a schematic drawing of another typical mechanical pulping equipment comprising multiple refiner stages.

It should be noted that the embodiment in FIG. 1a is only one example of a typical TMP process. The process stages and units may change places and many processes, e.g. the refining process can be performed more than once. Therefore, in FIG. 1b, another typical pulp manufacturing line is illustrated. This line resembles the one illustrated in FIG. 1a, except for the occurrence of double refiner stages. The pretreated wood is, here entered into a first refiner 212-1, where a coarse grinding takes place. The pulp is then entered into a unit 213 for adding of chemicals, e.g. dewatering agents, before it enters into a second refiner 212-2. The pulp exiting from the second refiner 212-2 then continues in a similar way as described in connection with FIG. 1a.

The refiner is the most important subprocess step in mechanical pulping and there exist, as discussed in the background, very clear economical benefits for implementation of a more advanced control of the refiner based on new information. In the refining process, wood is typically fed into a narrow gap between refiner discs. During their passage between the discs, the chips are defibrated and fibrillated. As indicated above, this can take place in one refiner or it can be partitioned into subsequent refiners. In the TMP refiner, the chips are pressurised and exposed to saturated steam. When the chips enters the refiner, the chip is first broken into small pieces, and the refining of these pieces takes place when they strike each other or any of the refiner discs. Centrifugal forces drives the coarse wood and pulp mixture outwards in radial direction, where the gap between the discs typically becomes smaller. The interaction defibrates and fibrillates the fibre material into the requested freeness level.

Since the interaction between the discs and the fibres are essential for the properties of the final pulp, parameters such as disc distance, disc rotational speed and force applied on the discs play an important role. Depending on the actual configuration of the refiner, such parameters are directly related to properties of the resulting pulp. By measuring the properties of the resulting pulp, the parameters can be fine adjusted in order to take care of deviations from specified pulp properties.

Furthermore, the collisions and friction between fibre and discs and between fibre and fibre consume a considerable amount of energy. This energy is also a parameter, which is of importance for the final pulp. The energy is transformed into heat, which increases the temperature of the pulp mixture and some of the water will evaporate into steam. The steam has a strong influence on the fibre flow within the refiner. The heat in the refining process changes the rheological properties of the wood and the fibres. The heat production and the water content thus also have an important influence on the final pulp quality, and are also parameters, which are of interest to be controllable.

Further aspects of process control in the refiner of mechanical pulping can be found e.g. in "Paper Making Science and Technology" Book No. 5: "Mechanical Pulping" by Kauko Leiviskä, ISBN 952-5216-05-5, pp. 129–138.

It is well known in the art that a number of pulp properties are influences by different settings of parameters for the refiner. A number of verified correlations have been found. In the case of fibre length, the disc speed is generally the most important refiner parameter. An increased disc speed generally resulted in longer fibres. In a similar manner, the freeness according to the Canadian Standard Freness (CSF) method has a correlation to the disc speed in that a higher disc speed results in a higher CSF freeness. A negative correlation is present for the total refiner power, i.e. a higher power generally results in a lower CSF freeness.

Figure 2:
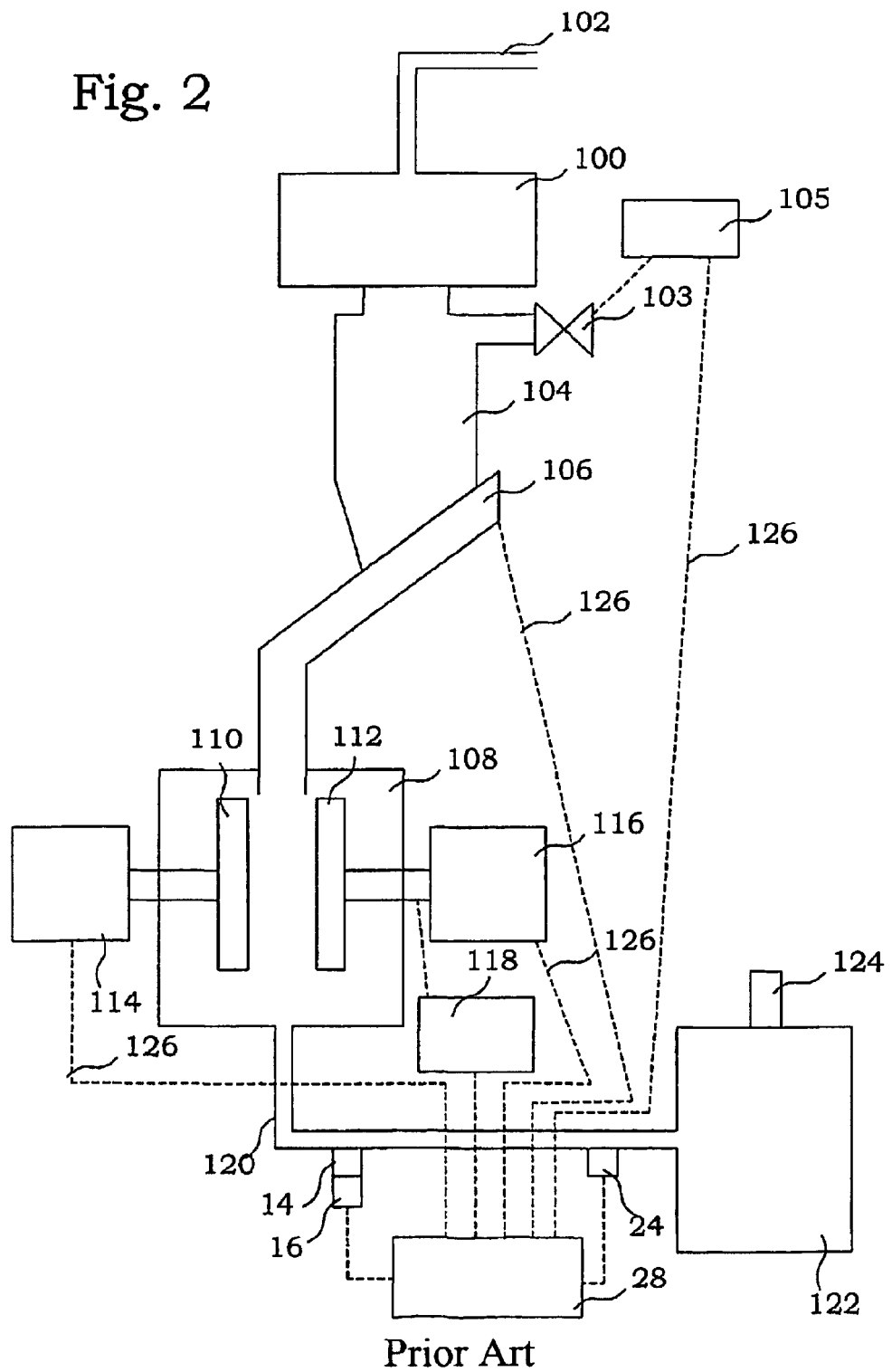
FIG. 2 is a schematic illustration of an embodiment of a pulp refiner line according to the present invention.

FIG. 2 illustrates a typical example of a refiner part of a mechanical pulping process system, such as described in FIG. 1. A pressurising unit 100 is supplied with pre-treated wood chips through a supply line 102. The pressurised chips are supplied to a container unit 104, where the chips are mixed with additional water 105. A screw device 106 brings the mixture with a certain determined rate into a refiner unit 108. The refiner 108 schematically illustrated in FIG. 72 comprises in this embodiment double discs 110, 112, between which the chip mixture is fed. Each disc 110, 112 has a respective motor 114, 116, which applies the necessary rotary motion to the refiner discs 110, 112. A refiner force control device 118 regulates the force with which the refiner discs 110, 112 are pulled together and the distance between the discs. The total energy fed into the refiner is also controllable.

After refining, the ground pulp fibres suspended in the water mixture exit the refiner at high pressure via an exit pipe 120. The high pressure is reduced, which causes some of the (by the refining process) heated water to evaporate into steam. The steam 124 is separated from the fibre mixture in a cyclone 122 before the fibres are introduced into the following pulping process steps.

Figure 3:
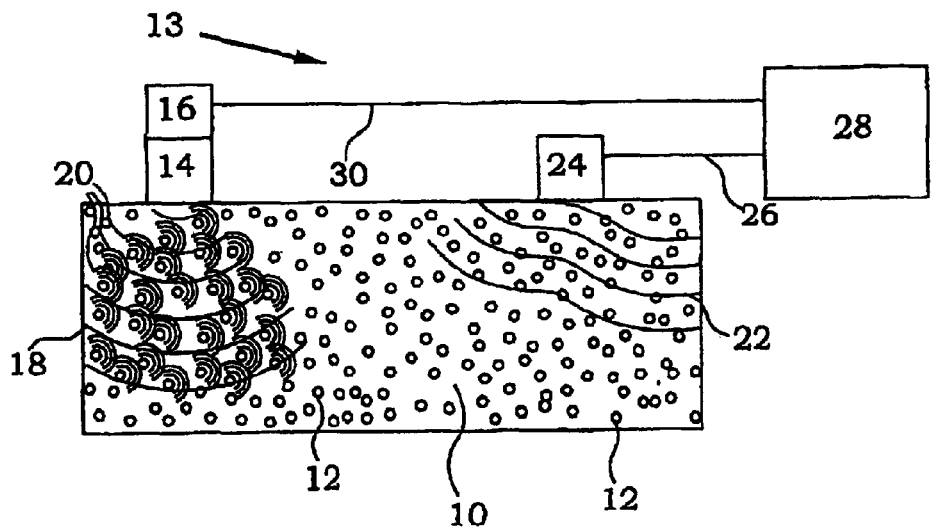
FIG. 3 is a schematic drawing of an analysing device used in the present invention.

FIG. 3 illustrates an analysing device 13 to be used in a refiner according to the present invention. A pulp mixture 10 comprises suspended fibres 12. An analysing device 13 is used to evaluate the properties of the pulp 10 and the fibres 12 therein. The analysing device comprises an emitter 14, which constitutes an acoustic signal source, and a control unit 16 for operating the emitter 14. The emitter 14 is arranged to emit acoustic signals into the pulp 10. Acoustic signals 18 are propagating as waves through the pulp 10 and will then be influenced by the presence of the suspended fibres 12.

This influence will, for waves with a wavelength much larger than the size of the fibres and distance between them, mainly manifest itself as a changed fluid compressibility. This will lead to a change in the phase speed and to absorption of the acoustic signals 18 which will be frequency dependent. In particular large changes can be expected in frequency ranges where the suspended particles 12 exhibit resonant vibration behaviour. The resonance frequencies depend e.g. on density, dimensions, stiffness, bonding within the fibre and bonding between fibres and many other properties. This frequency range is for almost all practical applications located in the audible subultrasonic region, i.e. below 20 kHz. Since the influence of even small particle concentrations, e.g. air bubbles in water, on fluid compressibility can be very large, a method based on long waved acoustic signals is potentially very sensitive for detecting fluid mixture variations. Of course this high sensitivity also implies that special measures might be needed to control any unwanted influence on the fluid properties. This can be achieved by applying special signal processing techniques, as discussed further below.

Furthermore, by using frequencies well below the ultrasonic range coherent signals can be provided making measurements of both amplitude and phase possible. This is described further in detail below.

The fibres 12 will thus influence the acoustic transmission properties (phase speed) of the process fluid and absorb vibration energy and thereby change the originally emitted acoustic signals. The vibrating fibres 12 will also themselves emit energy in the form of acoustic signals 20. These signals will typically be in the same frequency range as the fibre vibrations, i.e. in the frequency range below the ultrasonic range. The modified emitted acoustic signals 18 from the emitter 14 and the acoustic signals emitted from the fibres 20 will together form a resulting acoustic signal 22.

An acoustic signal sensor 24 is arranged at the system for measuring acoustic signals in the pulp 10. At least one component of the acoustic spectrum of the acoustic signals is measured. These acoustic signals are the resulting signals 22 from the interaction between the emitted acoustic signals 18 and the fibres 12. Since the interaction between acoustic signals and the fibres 12 is indicative of the nature of the fibres 12, the measured acoustic signals comprise information related to the fibres 12 suspended in the pulp fluid 10. The analysing device further comprises a processor 28, which is connected to the sensor 24 by a sensor connection 26. The processor 28 is an evaluation unit arranged for correlating the measured acoustic signals to properties, content or distribution of the fibres 12 within the pulp fluid 10. The emitter control unit 16 is preferably controllable by the processor 28 through an emitter connection 30 in order to tune or control the emitted acoustic signals dependent or co-ordinated with the measurement operation.

In a typical case, the processor 28 operates according to a certain model of the involved system. The model is preferably based on theories about the physical interaction between the fibres and the acoustic waves. The model or parameters in the model are calibrated by using a set of acoustic signal measurements and corresponding laboratory measurements of the fibre properties of interest. The model is then possible to use for predicting the fibre properties from acoustic spectra of unmown samples.

Now returning to FIG. 2; an emitter 14 with a control unit 16 is arranged at the exit pipe 120. A sensor 24 is also arranged at the exit pipe a distance from the emitter 14. The emitter 14 and sensor 24 are connected to an evaluation unit 28 comprising a processor. The emitter 14 is controlled to emit acoustic signals into the pulp mixture within the exit pipe 120. The sensor 24 records the resulting acoustic signals and the processor 28 evaluates the results.

Paper strength issues are a vast area with many different laboratory measurement methods and evaluation possibilities. Nevertheless, it is probably the most common and important quality parameter demanded by the customers. Basically, the final paper strength (S) can be described by three parameters; the single fibre intrinsic strength (z), the area of fibre-to-fibre bond per length unit of the fibre (n) and the strength of each fibre bond (p). A relation:

$$S = fkn(z,n,p)$$

may be determined. Longer fibres will provide opportunities for more fibre-to-fibre bonds and therefore the fibre network will be stronger and consequently also the paper. This is naturally a simplification of reality where also other parameters play an important role. If the fibres are excited, they vibrate with different frequencies depending on their length. The point of self oscillation will be at a lower frequency for long fibres compared to short ones. In reality, the fibres in pulp will obtain a fibre length distribution and their natural vibration will be within a frequency band with the highest amplitude for the frequency corresponding to the median fibre length. Thus, acoustic measurements are suitable for detection of fibre length distribution.

One of the most important parameters for the papermaking concerning runnability of the paper machine is the drainage characteristics of the pulp on the wire. The paper maker generally run the paper machine as fast as possible. If the dry line, i.e. the place on the wire where the visible water on the paper web disappears due to dewatering, comes too close to the press section, e.g. due to decreased dewatering characteristics of the pulp, a web break is likely to appear, which stops the production and causes huge economical losses. Bad dewatering forces the papermaker to run the paper machine more slowly which causes lower production. Basically the dewatering capacity (d) of the pulp can be explained by two parameters; the fibre flexibility (f) and the fibre size distribution described as the numerical relationship between the amount of long fibres divided with the amount of short fibres (q). An approximate relation $$d = fkn(1/f, q)$$

is possible to establish. Dewatering characteristics is also correlated to the final paper strength. If the fibre size distribution is the same, flexible fibres will obtain larger bonding areas between each other. Thus a higher paper strength can be obtained. Simultaneously, a network of more flexible fibres will be more difficult to dewater. Generally, a fibre network dominated by short fibres or fines also will be more difficult to dewater compared to one consisting of longer fibres. From an acoustic point of view, the stiff fibres have a higher natural vibration than the flexible ones. Similar to the example above, there will be a distribution of fibres in the pulp with different flexibilities and acoustic measurement will record a frequency band with the highest amplitude for the frequency corresponding to the median fibre flexibility. Thus, acoustic measurements are obviously suitable for detection of fibre flexibility.

Furthermore, the water amount can also be monitored, since the total strength of characteristic features in the acoustic signals are depending on the concentration of the pulp within the mixture. Several aspects of the pulp mixture may thus be monitored by the analysing device.

The above properties of the refined pulp are determined by certain input parameters in the refining process. Parameters which determines the effect of the refining is e.g. the water content, addition of dewatering agents, the rate in which the chips are entered into the refiner, the refiner power, the disc velocity and the force and distance between the refiner discs 110, 112. The relations between these parameters and the properties of the pulp are normally rather well known, or may be obtained empirically. Based on such relations, the analysing device 13 may find appropriate changes in the settings of the refiner power disc speed disc force disc distance water content, dewatering agents or chip feeding speed by signal connections 126 in order to improve the properties of the resulting fibres. The analysing device thus constitutes a feed-back system, operating on the final process fluid from the refiner subprocess.

Experiments have been performed, investigating the correlation between acoustic spectrum and pulp quality. Acoustic spectra were measured from a number of pulp fluids, and samples of the pulp fluids were analysed in a laboratory according to a standard method for Canadian Standard Freeness (CSF) and mean fibre length according to the Kajaani instrument. The acoustic spectra were recorded and Fourier transformed into discrete spectrum channels, with intensity as a function of frequency. The spectra were evaluated using multivariate data analysis. In the interpretation of qualitative information relating to pulp quality parameters, the PLS models calculated are supposed to filter out noise related to calibration errors etc. The quality of the models can therefore be evaluated as their ability to predict pulp quality from spectral data and is expressed as a root mean square error of cross validation, RMSECV, Low RMSECV and a high number of explained PLS parameters are desirable. A more detailed description of such data analysis is to be found in 'Multivariate Calibration' by H. Martens and T. Naes, John Wiley & Sons, Chicester, 1989, pp. 116–163.

Figure 4:
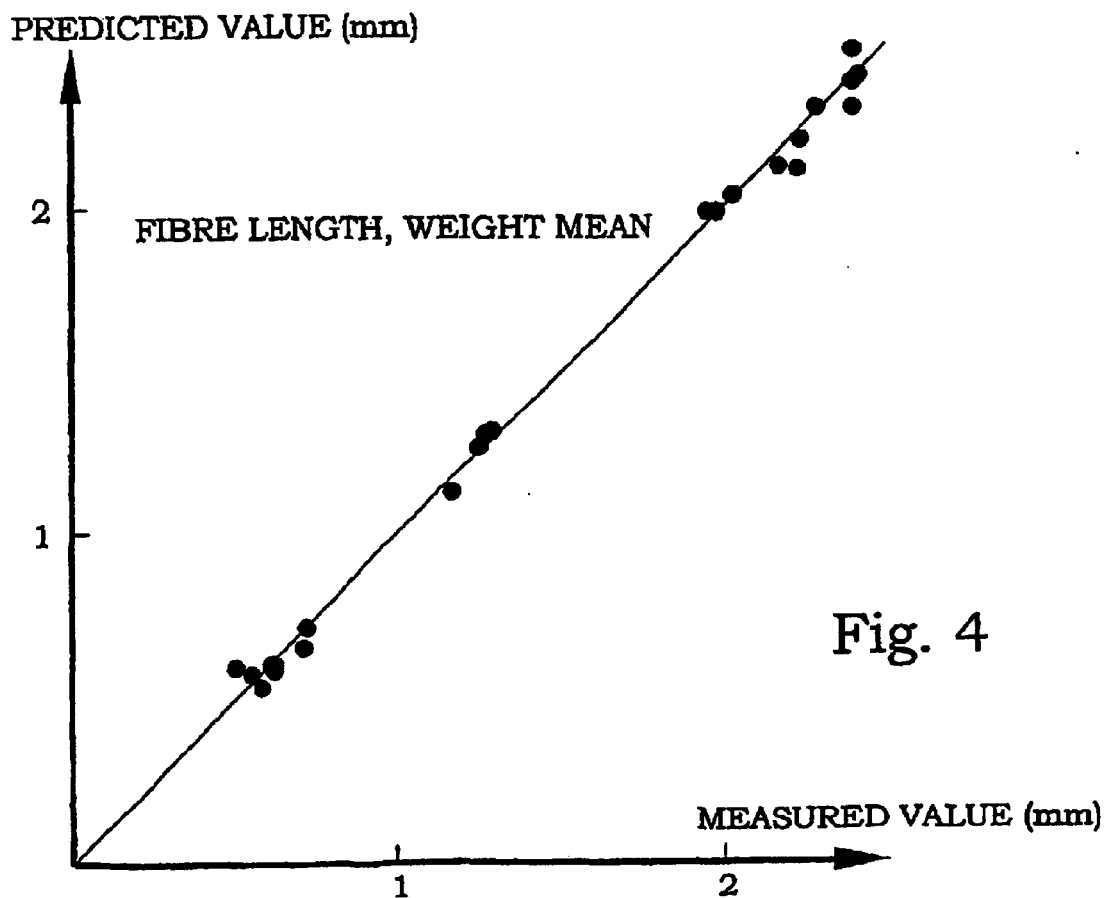
FIG. 4 is a diagram illustrating a typical correlation between actual and correlated properties of pulp in a test setup.

FIG. 4 illustrates a typical result from a model for prediction of fibre length. A model is calibrated using pulp samples with known fibre length. When the calibrated model then is used to predict values of the fibre length, the result looks like the one shown in diagram 4. At the horizontal axis, the true (measured by conventional laboratory methods) value of the weight mean fibre length is noted, at the vertical axis, the fibre length predictions using acoustic measurements are given. There is an obvious linear relation between the "true" and predicted values, with a relatively good correlation.

Figure 5:
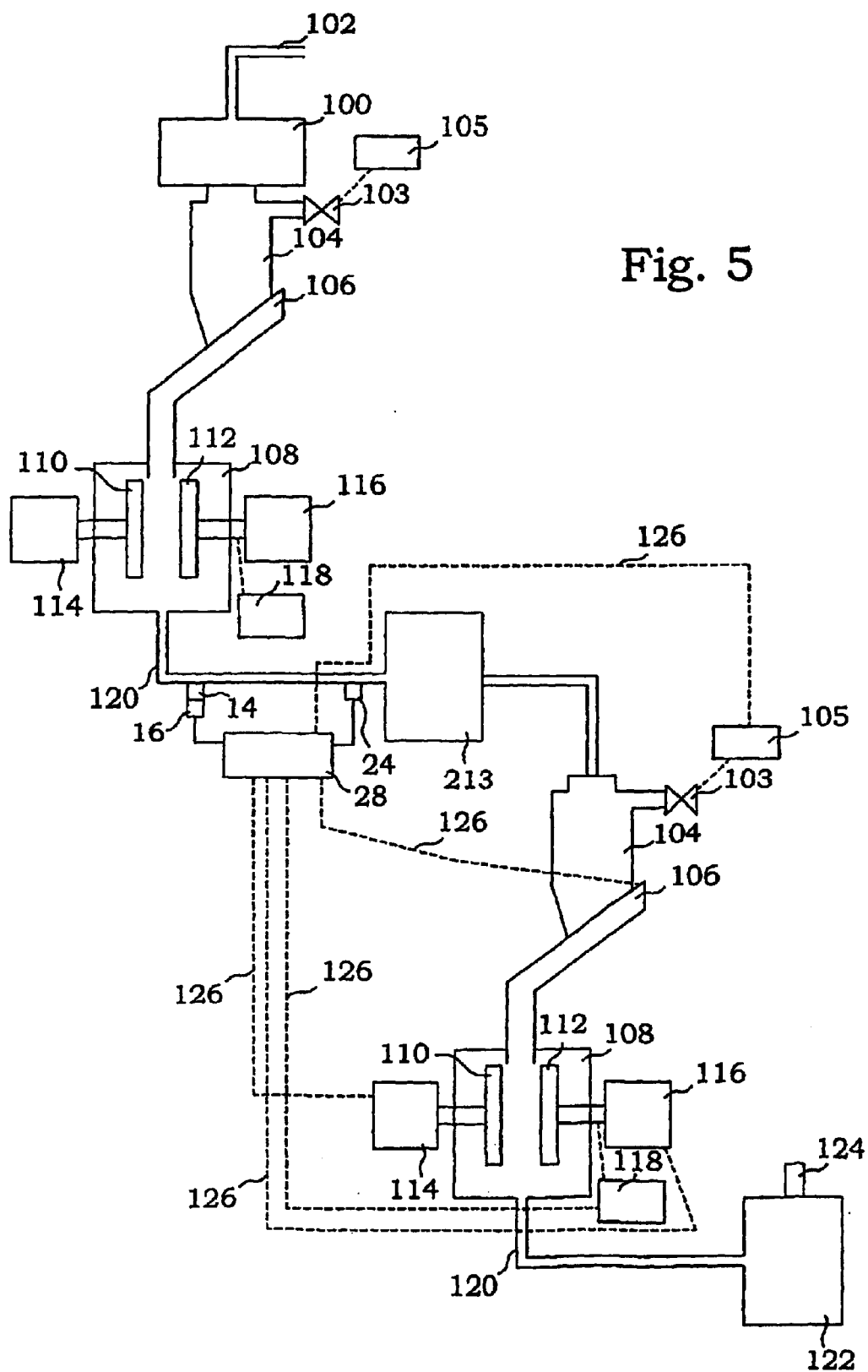
FIG. 5 is a schematic illustration of another embodiment of a pulp refiner line according to the present invention.

FIG. 5 illustrates another embodiment of refiner equipment according to the present invention. This embodiment corresponds to the configuration in FIG. 1b. Parts, which are identical to the ones shown in FIG. 2, have the same reference numbers. Identical parts will not be discussed again. In this embodiment, the refining stage comprises two subsequent refiners separated by a unit for adding dewatering agents 213. In FIG. 5, an emitter 14 with a control unit 16 is arranged at the exit pipe 120 from the first refiner 108. A sensor 24 is also arranged at the exit pipe a distance from the emitter 14. The emitter 14 is controlled to emit acoustic signals into the pulp mixture within the exit pipe 120. The sensor 24 records the resulting acoustic signals and the processor 28 evaluates the results. The evaluation unit 28 is connected by control connections 126 to the different control units of the second refiner equipment.

This configuration allows for a monitoring of the rough pulp material entering the second refiner, i.e. is arranged upstream from the second refiner. In this way it is possible to detect changes in the rough pulp material, e.g. different kinds of pulp quality, water content, mean fibre lengths and freeness. Depending on the properties of the pulp entering into the second refiner, requested properties of the pulp resulting from the total refiner process may be obtained by operating the second refiner slightly different. Harder wood normally requires a higher disc speed, while chips with a lot of moisture need a less amount of added water in order to achieve optimum properties of the produced pulp. The total refiner operation can according to the present invention be adjusted to the properties of the rough pulp material fed into the second refiner. A feed-forward control is thus accomplished.

Obviously, these two different embodiments can be combined in any configuration.

Figure 6:
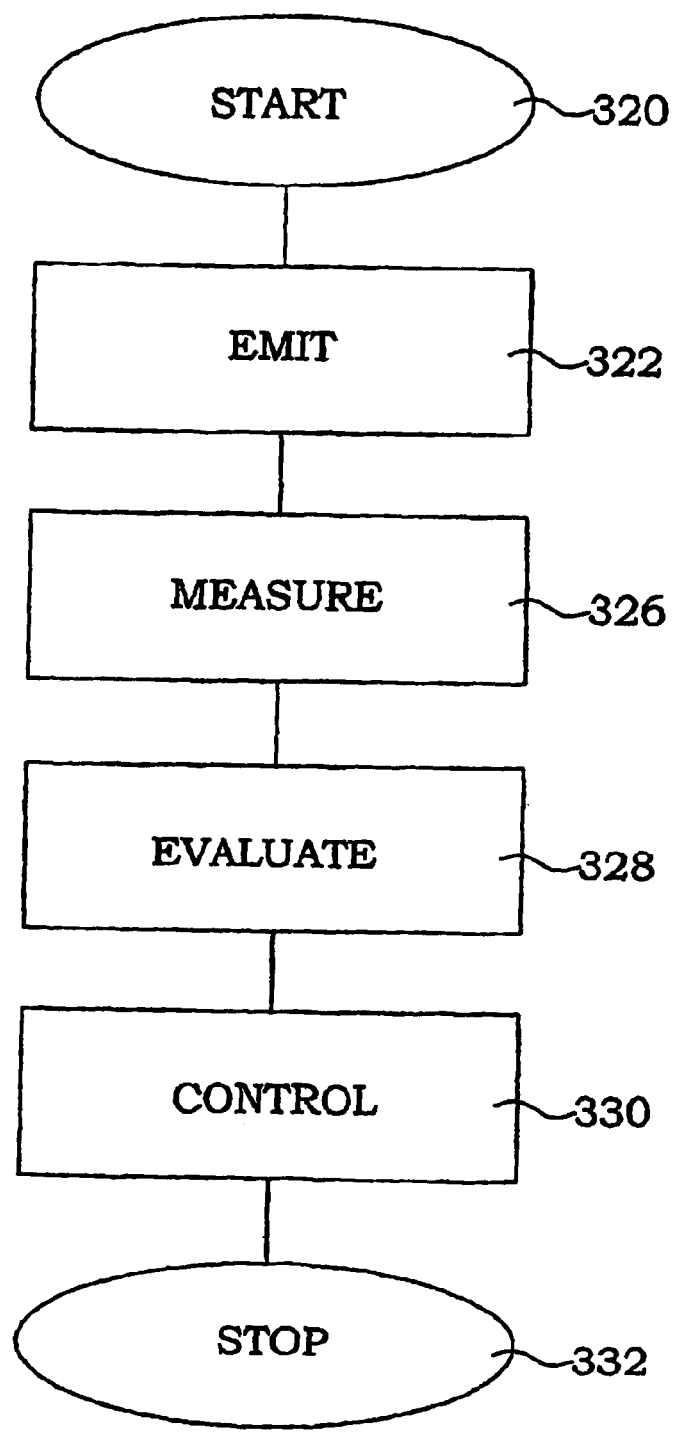
FIG. 6 is a flow diagram of a refiner control method according to the present invention.

A corresponding method for refiner control is illustrated in the flow diagram of FIG. 6. The procedure starts in step 320. In step 322, an acoustic signal of sub-ultrasonic frequencies is emitted into a pulp fluid comprising suspended fibres. The acoustic signals interact with the suspended fibres and give rise to a resulting acoustic signal. This resulting acoustic signal is measured in step 326 and in step 328, the measurement results are evaluated, preferably in terms of properties of the fibres in the pulp. The evaluated properties are preferably mechanical or chemical data, concentrations, distributions and sizes of the fibres. Theses properties are in step 330 used for controlling a refiner process. The procedure ends in step 332.

The controllability of the acoustic source is very important. By selecting amplitude, frequency, phase and/or timing of the acoustic signals, different properties of the fibres can be addressed. By controlling the frequency, the acoustic signals may e.g. be tuned to certain resonance frequencies connected to the fibres, addressing specific properties. By modulating the amplitude of the signal source, noise reduction may be performed, or time dependent interactions may be emphasised or suppressed. By controlling the phase, dynamic measurements are facilitated. By controlling the timing of the acoustic signals, processes having time dependencies may be investigated. Such investigations are not possible to perform using only passive sources of acoustic signals. A few examples of simplified situations will illustrate the possibilities of controlling the signal source.

Figure 7A:
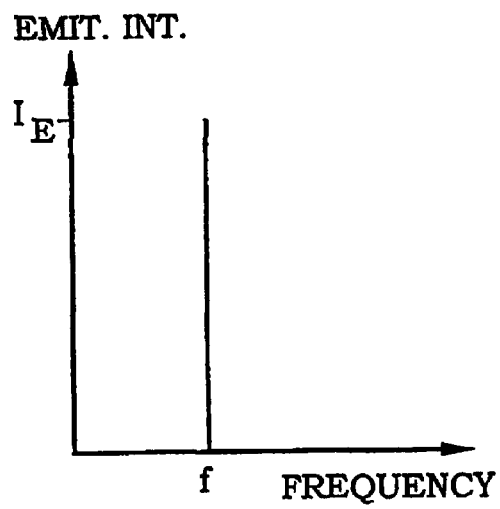
Figure 7B:
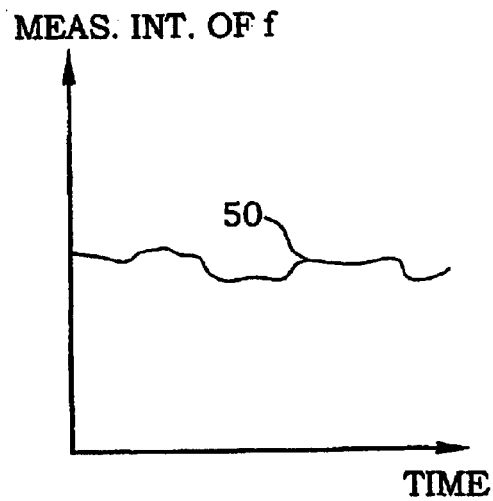

In FIG. 7a, the signal source emits an acoustic signal having one frequency f of intensity $I_E$. The frequency is tuned into a certain frequency corresponding to a characteristic frequency of the particles, e.g. an absorption frequency of particles within the process fluid. The lagger density of particles, the larger absorption will result. The acoustic signal is emitted with a constant intensity $I_E$ for the time the measurement lasts. By measuring the intensity 50 of the same frequency component of the resulting acoustic signal from the process fluid as a function of time, an indication of the particle density variation with time will be obtained. This is schematically illustrated in FIG. 7b. Using such a measurement, a concentration monitoring is easily performed and by introducing an interval of permitted variations, the signal may easily be used as an indicator of a too high or too low concentration.

Figure 7C:
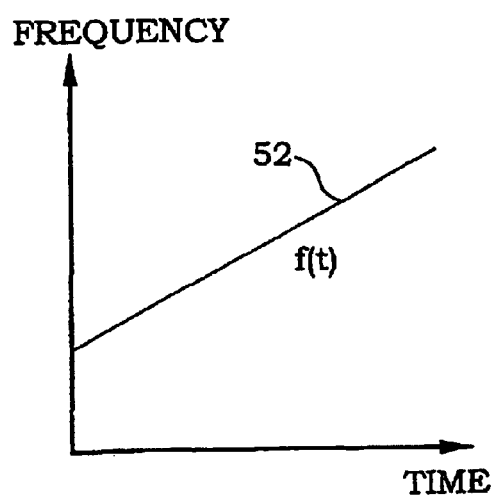
Figure 7D:
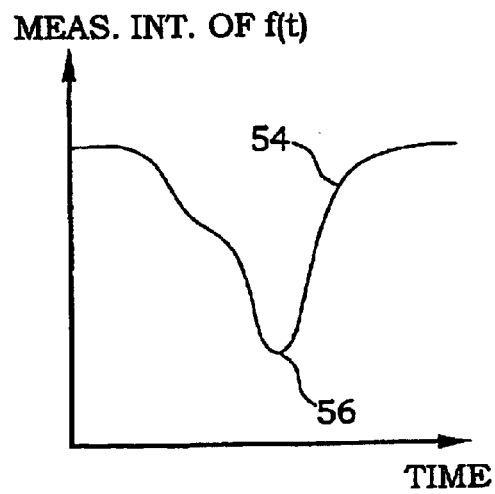

Assuming a process fluid having solid particles of slightly differing dimensions. Knowing that a certain resonance vibration is related to a certain dimension of the particle can be used to investigate the size distribution of the particles in the fluid. FIG. 7c illustrates a time dependent emitted acoustic signal. The amplitude or intensity of the signal is kept constant, while the frequency is varied linearly with time, as illustrated by the line 52 in FIG. 7c. The sensor can be operated in a coordinated manner, measuring the intensity of the same frequency that the acoustic source at each occasion emits. In that way, a resulting curve 54 as illustrated in FIG. 7d may be obtained. An intensity minimum 56 at the curve 54 indicates that this frequency corresponds to the median value of the dimension in question. Information about the size distribution is also obtainable.

In this manner, the frequency can be used for revealing different aspects related to the particles. The frequency may thus comprise e.g. a single constant frequency, a single frequency varying with time, a number of single constant frequencies, a number of single frequencies varying with time, or different types of limited frequency bands, such as white or pink noise.

Figure 7E:
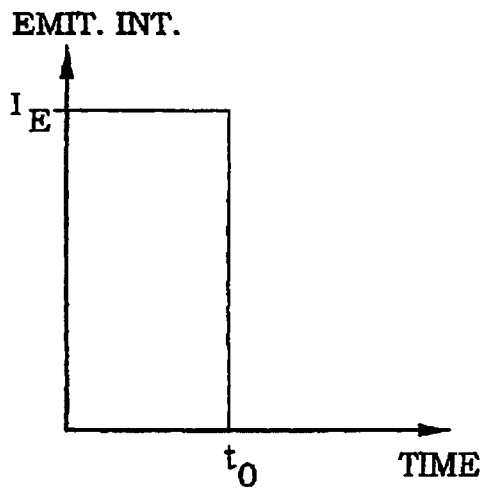
Figure 7F:
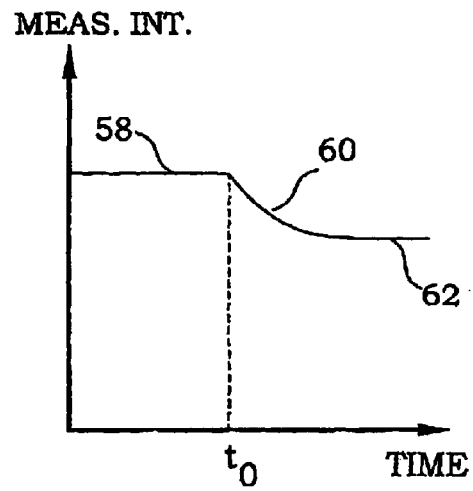

The timing of the emitted acoustic signals may also be used, e.g. by using pulsed acoustic signals emitted during limited time intervals. FIG. 7e illustrates a simplified situation where an acoustic signal is emitted during a time interval up to the time to, when the emission is turned off. By measuring e.g. an intensity of some acoustic signal features, a curve illustrated in FIG. 7f may be obtained. This curve presents a constant level portion 58 during the time the pulse is emitted. When to is reached, the intensity starts to decrease creating a reverberation process, as shown in the portion 60, until the intensity levels out at 62. An interpretation of this behaviour could e.g. be that inherent noise within the system gives rise to an intensity of the signal feature corresponding to the level of the portion 62. This intensity would therefore correspond to background noise. Background signals in the measured acoustic signals may be reduced simply by subtracting acoustic signals measured during time intervals, in which the controllable acoustic source is inactive. The intensity difference between the portions 58 and 62 would therefore more accurately correspond to e.g. some concentration values of particles within the fluid. The detailed behaviour of the decreasing portion 60 may also give some information about e.g. mechanical interaction conditions within or around the particles. The slope could e.g. correspond to remaining vibrating particles after the turn-off of the acoustic source.

Figure 7G:
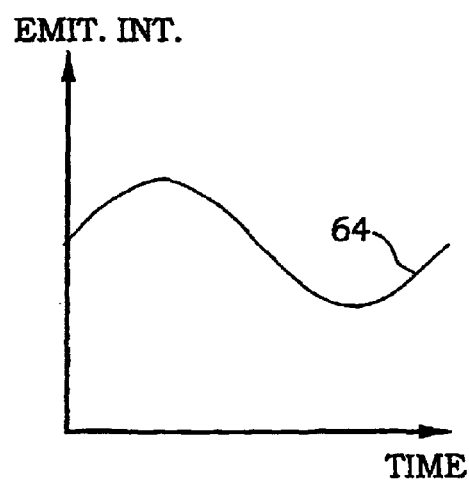
Figure 7H:
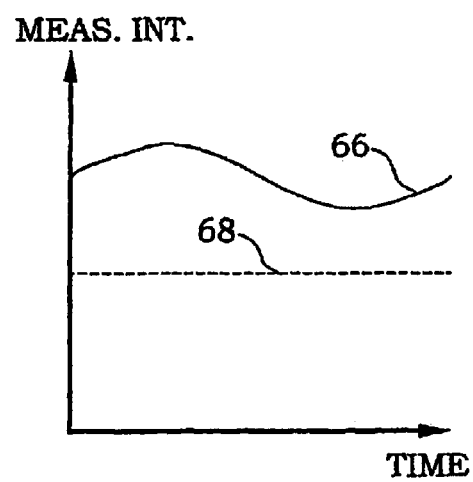

More sophisticated background reduction methods would be available by amplitude modulating the emitted acoustic signal. In FIG. 7g, the intensity of an emitted acoustic signal is varied with time according to the curve 64. A corresponding measured intensity of any acoustic spectrum feature could then vary e.g. as the curve 66 in FIG. 7h. The intensity variation is less pronounced, which implies that a background noise probably is present. By comparing the amplitude variations of the emitted and sensed signals, a background level according to the broken line 68 is found. Thus, background reduction is possible to perform also with continuously emitted signals.

The background signals may themselves comprise interesting information. By following the evaluation of the background signals during a somewhat longer time period, changes may be detected. Such changes or trends of the measured acoustic signals may e.g. be correlated to ageing or wearing changes in the refiner equipment, in particular the disks, and the background evaluation information may therefore e.g. be used to indicate maintenance needs etc.

From the above examples, it is obvious that the sensors should be able to measure different properties of the resulting acoustic signals. In a corresponding manner as for the emitted signals, the sensors measures e.g. amplitude, frequency, phase and/or timing of the acoustic signals resulting from the interaction with the particles in the process fluid. It is preferred if the sensors may measure at least three of the above mentioned characteristics, since a robust multivariate analysis then can be performed. The use of more variable dimensions is illustrated by a simplified example.

Assume an emitted acoustic signal according to FIG. 7c. A sensor measures an acoustic spectrum within a certain frequency interval at a number of successive times during the emission frequency scan. A possible result is shown in FIG. 7i. Two main components are present in the resulting spectrum. A first component 72 follows the emitted frequency, and a second component 70 is constant in frequency. The result indicates that the particles have a resonance frequency corresponding to a minimum intensity (max absorption) of the first component 72. However, when the emitted frequency corresponds to the second component 70, the two signals are superimposed and an intensity curve like in FIG. 7d would show a peculiar behaviour. However, following the evaluation of the spectra, the different features are easily distinguished and a correct analysis may be obtained.

The above examples are only given as oversimplified examples to increase the understanding of the possibilities of a system with controllable active acoustic sources. In real cases the situations are far more complicated and multivariate statistical analysis or neural networks are for instance used to evaluate the measured acoustic spectra.

The recorded acoustic spectra are preferably Fourier transformed to obtain intensity variations as a function of frequency. The acoustic spectra are then preferably analysed using different kinds of multivariate data analysis. The basics of such analysis may e.g. be found in "Multivariate Calibration" by H. Martens and T. Naes, John Wiley & Sons, Chicester, 1989, pp. 116–163. Commercially available tools for multivariate analysis are e.g. "Simca-P 8.0" from Umetrics or PLS-Toolbox 2.0 from Eigenvector Research, Inc. for use with MATLAB™. PLS (Partial Least Square) methods of first or second order are particularly useful. Neural network solutions, such as Neural Network Toolbox for MATLAB™, are also suitable to use for analysis purposes.

To improve the model predicting ability, a pre-treatment of spectral data is sometimes beneficial. Such a pre-treatment can include orthogonal signal correction or wavelength compression of data. Furthermore, both the real and imaginary part of the acoustic signal can be used in multivariate calculations.

Figure 8A:
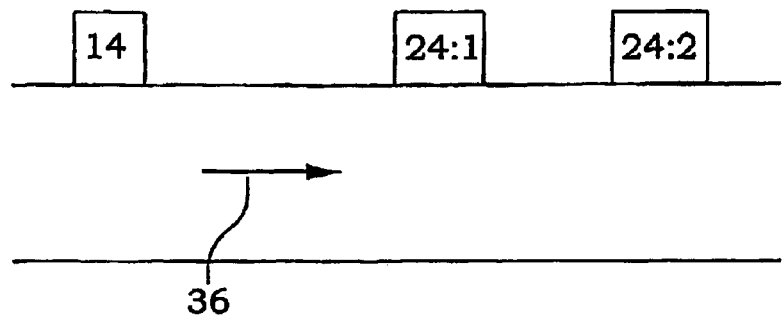
FIGS. 8a–8c are schematic drawings illustrating sensor array configurations.

The relative geometrical positioning and/or the number of emitters and/or sensors can also be used to increase the reliability of the measured signals and thereby the properties of the particles. In FIG. 8a, a pulp flow is directed in the direction of the arrow 36. An emitter 14 is arranged in the upstream direction. Two sensors, 24:1, 24:2, are located downstreams at different distances from the source. By using measurements from both sensors, additional information may be obtained. One obvious possibility is to measure the propagation speed of the acoustic signals within the pulp or the flow rate, by measuring the phase shift or the time delay between the two measurements. Such information can support the interpretation of other results and may even contain its own information, e.g. the concentration of fibres. The distance between the sensors is preferably in the same order of magnitude as the acoustic wavelength to allow for phase measurements. It would also be possible to detect time dependent properties of the fibres. If fibres are vibration excited or influenced in any other way of a acoustic pulse when passing the emitter, and the result from this excitation or influence will decay with time, the two sensors 24:1 and 24:2 will detect different time behaviour of their measurements. From he differences, information about decay times etc. may easily be obtained by computer supported analysis.

Figure 8B:
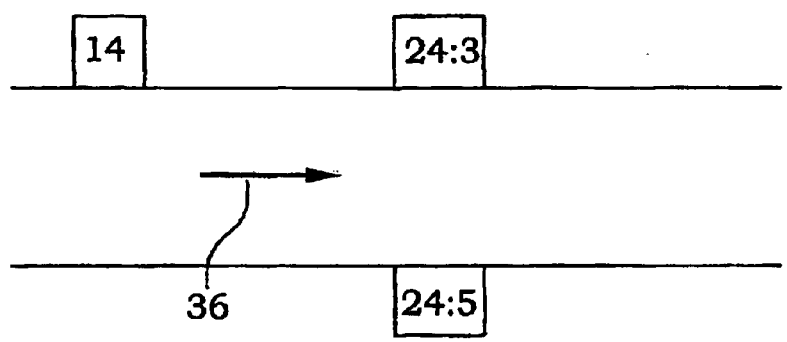
Figure 8C:
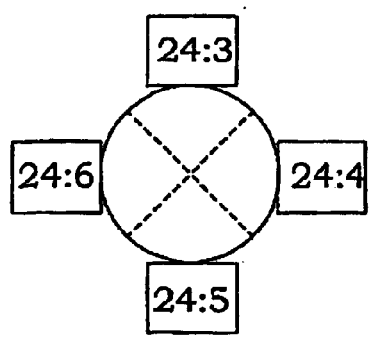

The positioning of sensors can be used also in other ways. In FIG. 8b, a system containing four sensors, of which two are shown in the sectional view along the flow direction, is illustrated. In FIG. 8c, a corresponding cross-sectional view is illustrated. The four sensors 24:3, 24:4, 24:5 and 24:6 are positioned in a plane perpendicular to the flow path 36, asymmetrically with respect to the emitter 14, but symmetrically around the pipe enclosing the pulp flow path 36. By adding and subtracting signals from the four sensors located at one plane it is possible to extract up to four different acoustic wave types (modes). In addition a combination of the arrangements in FIGS. 6a and 6b is possible.

The acoustic signal emitter can be of different types. For higher frequencies, up to the audible limit, crystal transducers can be used. For low and intermediate frequencies, more specially constructed sound sources has to be used. One possibility is e.g. to use an electrodynamic shaker driving a membrane or a light-weight piston.

Sensors, detecting acoustic signals, are readily available in the prior art. Since the quantity of primary interest here is fluctuating pressure, the best alternative is probably to use pressure sensors or transducers. For applications in gases at normal temperatures (<70° C.) standard condenser or electric microphones are preferably used. Some well-known manufacturers are Bruel&Kjaer, Larson&Davies, GRAS and Rion. These microphone types are sensitive and accurate, but for applications in hot or dirty environments they must be cooled and protected. Also very high levels (>140 dB) can be a problem. An alternative for hot and difficult environments is piezoelectric pressure transducers. These are much more expensive than condenser microphones but can be used up to temperatures of several hundred degrees Celsius. Drawbacks are that the pressure sensitivity is much lower than for condenser microphones and that this transducer type can pick up vibrations. An advantage is that many piezoelectric transducers can be used both in liquids and gases. However, special types for liquids also exist and are normally called hydrophones. A leading manufacturer of piezoelectric transducers is Kiestler.

If measuring the pressure, the sensor has to be in direct contact with the fluid. However, this has some obvious disadvantages since it is necessary to make a hole in a pipe or wall for mounting purposes. An alternative choice of sensors is vibration sensors, which can be mounted on a wall and measure the vibrations induced by the acoustic signals. Here, no direct contact with the fluid is required, why the mounting can be made more flexible and protected. However, a wall mounted vibration transducer will also pick up vibrations caused by other means, e.g. by machines comprised in the system. To some extent these wall vibrations will also radiate sound waves into surrounding fluid, which could be picked up by a pressure transducer, but normally this effect represents a much smaller disturbance.

In cases where both amplitude and phase measurements are of interest, further dimensional limitations are put on the sensors and frequencies. In order to be able to detect the phase of an acoustic signal, the sensor has to have a size that is small compared with the wave length of the acoustic signals. This puts in practice an upper limit of the frequency that can be used. If, as an example, the phase is going to be measured by a sensor of around 1 cm in size, the wavelength of the acoustic signal should be in the order of at least 15 cm. The speed of sound in e.g. water is in the order of 1500 m/s, which means that a maximum frequency of 10 khz can be used. Smaller sensor sizes allows higher frequencies.

Regarding vibration transducers, the standard choice for all frequencies used in the present invention is so called accelerometers, which typically are piezoelectric sensors that gives an output proportional to acceleration. Regarding manufacturers the ones already listed for condenser microphones also apply in this case.

The method according to the present invention may be implemented as software, hardware, or a combination thereof. A computer program product implementing the method or a part thereof comprises a software or a computer program run on a general purpose or specially adapted computer, processor or microprocessor. The software includes computer program code elements or software code portions that make the computer perform the method using at least one of the steps previously described in FIG. 6. The program may be stored in whole or part, on, or in, one or more suitable computer readable media or data storage means such as a magnetic disk, CD-ROM or DVD disk, hard disk, magneto-optical memory storage means, in RAM or volatile memory, in ROM or flash memory, as firmware, or on a data server.

It will be understood by those skilled in the art that various modifications and changes may be made to the present invention without departure from the scope thereof, which is defined by the appended claims.

REFERENCES

D. J. Adams: "Ultrasonic propagation in paper fibre suspensions", 3rd International IFAC Conference on Instrumentation and Automation in the Paper, Rubber and Plastics Industries, p. 187–194, Noordnederlands Boekbedrijf, Antwerp, Belgium.

M. Karras, E. Harkonen, J. Tornberg and O. Hirsimaki: "Pulp suspension flow measurement using ultrasonics and correlation", 1982 Ultrasonics Symposium Proceedings, p. 915–918, vol. 2, Ed: B. R. McAvoy, IEEE, New York, N.Y., USA.

International patent application WO99/15890.

H. Martens and T. Naes: "Multivariate Calibration", John Wiley & Sons, Chicester, 1989, pp. 116–163.

What is claimed is:

1. A pulp refiner control method, comprising:
    emitting a controllable acoustic signal into a pulp fluid for interaction of the controllable acoustic signal with fibers in the pulp fluid;
    tuning the controllable acoustic signal to characteristic frequencies of the fibers;
    measuring acoustic signals from the pulp fluid, the measuring comprising measuring at least one spectral component resulting from the interaction of the controllable acoustic signal and the fibers;
    determining at least one process control parameter based on the measured acoustic signals; and
    controlling a refiner process treating the pulp fluid.

2. The method according to claim 1, wherein determining at least one process control parameter comprises predicting from the measured acoustic signals properties of the fibers in the pulp fluid, thereby providing process control parameters for the refiner process.

3. The method according to claim 2, wherein at least one of the properties of the fibers is selected from the list of:
    mechanical property,
    chemical property,
    concentration
    shape, and
    size.

4. The method according to claim 1, wherein measuring acoustic signals from the pulp fluid is performed downstream relative to the refining process, providing a feed-back of the result of the refining process.

5. The method according to claim 1, wherein measuring acoustic signals from the pulp fluid is performed upstream relative to the refining process, providing a feed-forward from the pulp fluid entering the refining process.

6. The method according to claim 1, wherein the emitted acoustic signal comprises acoustic waves having a large wavelength compared to a typical size of the fibers, and a typical distance between the fibers.

7. The method according to claim 1, wherein the at least one spectral component has a frequency below 20 kHz.

8. The method according to claim 1, wherein controlling the refiner process comprises controlling at least one parameter of the following list:
    rate of entering chips/pulp,
    distance between refining disks,
    water addition flow,
    pressure on refining disks,
    refiner speed,
    addition of dewatering agents, and
    refiner power.

9. The method according to claim 1, further comprising:
evaluating trends of measured acoustic signals for detecting aging information of refining disks.

10. The method according to claim 1, wherein measuring at least one spectral component comprises measuring for at least one frequency at least one of the properties in the list of:
amplitude,
phase, and
time-delay.

11. The method according to claim 10, wherein measuring at least one spectral component comprises measuring for at least one frequency at least two of the properties in the list of:
amplitude,
phase, and
time-delay.

12. The method according to claim 1, wherein the controllable acoustic signal is pulsed and emitted during time intervals.

13. The method according to claim 1, further comprising:
amplitude modulating the controllable acoustic signal; and
reducing background signals in the measured acoustic signals, based on the amplitude modulation.

14. The method according to claim 1, wherein the predicting comprises multivariate statistical analysis of the measured acoustic signals.

15. A pulp refiner control method, comprising:
emitting a controllable acoustic signal into a pulp fluid for interaction of the controllable acoustic signal with fibers in the pulp fluid;
measuring acoustic signals from the pulp fluid, wherein the measuring comprises measuring at least one spectral component resulting from the interaction of the controllable acoustic signal and the fibers;
determining at least one process control parameter based on the measured acoustic signals, wherein the determining at least one process control parameter comprises predicting from the measured acoustic signals properties of the fibers in the pulp fluid, thereby giving process control parameters, and wherein the predicting comprises predicting from the measured acoustic signals properties of paper manufactured by the pulp; and
controlling a refiner process treating the pulp fluid.

16. An apparatus for analysis of a pulp fluid comprising:
an acoustic signal source arranged to emit a controllable acoustic signal into the pulp fluid for interaction with the fibers;
a control operative to control the acoustic signal source, wherein the control comprises a tuner operative to tune at least one frequency of the controllable acoustic signal to characteristic frequencies of the fibers;
an acoustic signal sensor for measuring acoustic signals from the pulp fluid, wherein the acoustic signal sensor is arranged to measure at least one spectral component resulting from the interaction of the controllable acoustic signal and the fibers; and
a data processor connected to the acoustic signal sensor and operative to predict mechanical/chemical properties of fibers in the pulp fluid based upon the measured acoustic signals.

17. A refiner apparatus for handling a pulp fluid, the apparatus comprising:
an acoustic signal source arranged to emit a controllable acoustic signal into the pulp fluid for interaction with fibers in the pulp fluid;
control means for controlling the acoustic signal source, the control means comprising means for tuning the controllable acoustic signal to characteristic frequencies of the fibers;
an acoustic signal sensor for measuring acoustic signals from the pulp fluid, wherein the acoustic signal sensor is arranged for measuring at least one spectral component resulting from the interaction of the controllable acoustic signal and the fibers in the pulp fluid;
data processing means comprising a processor and being connected to the acoustic signal sensor for determining at least one process control parameter based on the measured acoustic signals;
means for carrying out a refiner process of the pulp fluid; and
process control means for controlling the means for carrying out a refiner process according to the determined at least one process control parameter.

18. The apparatus according to claim 17, wherein the data processing means is further arranged for predicting from the measured acoustic signals properties of the fibers in the pulp fluid.

19. The apparatus according to claim 17, wherein the acoustic signal sensor is positioned downstream relative to the means for carrying out the refiner process, thereby providing a feed-back of the result of the refiner process.

20. The apparatus according to claim 17, wherein the acoustic signal sensor is positioned upstream relative to the means for carrying out the refiner process, thereby providing a feed-forward from the process fluid entering the refiner process.

21. The apparatus according to claim 17, wherein the process control means comprises means for controlling at least one of the parameters of the following list:
rate of entering chips/pulp,
distance between refining disks,
water addition flow,
pressure on refining disks,
refiner speed,
addition of dewatering agents, and
refiner power.

22. The apparatus according to claim 17, further comprising:
means for evaluating trends of measured acoustic signals for detecting aging information of the refining disks.

23. The apparatus according to claim 18, wherein at least one of the properties of the fibers is selected from the list of:
mechanical property,
chemical property,
concentration,
shape, and
size.

24. The apparatus according to claim 17, wherein the acoustic signal sensor has a small size compared to the wavelength of waves emitted by the acoustic signal source.

25. The apparatus according to claim 17, wherein the acoustic signal sensor is operable for frequencies below 20 kHz.

26. An apparatus for analysis of a pulp fluid comprising:
an acoustic signal source arranged to emit a controllable acoustic signal into the pulp fluid for interaction with the fibers;
a control operative to control the acoustic signal source;
an acoustic signal sensor for measuring acoustic signals from the pulp fluid, wherein the acoustic signal sensor is arranged to measure at least one spectral component resulting from the interaction of the controllable acoustic signal and the fibers, the at least one spectral component including at least two properties selected from the list of amplitude, phase, and time-delay; and a data processor connected to the acoustic signal sensor and operative to predict mechanical/chemical properties of fibers in the pulp fluid based upon the measured acoustic signals.

27. An apparatus according to claim 26, wherein the control comprises means for tuning the controllable acoustic signal to characteristic frequencies of the fibers.

28. The apparatus according to claim 26, wherein the control comprises means for causing the acoustic signal source to emit during limited time intervals.

29. The apparatus according to claim 26, wherein the control further comprises amplitude modulation means for the controllable acoustic signal and wherein the apparatus further comprises means for reducing background signals in the measured acoustic signals, connected to the control, for receiving information about the amplitude modulation.

30. The apparatus according to claim 26, wherein the data processor is further arranged for predicting, from the measured acoustic signals, properties of paper manufactured by the pulp.

31. The apparatus according to claim 26, wherein the data processor comprises means for multivariate statistical analysis of the measured acoustic signals.

32. An apparatus for analysis of a pulp fluid comprising:

an acoustic signal source arranged to emit a controllable acoustic signal into the pulp fluid for interaction with the fibers;

a control operative to control the acoustic signal source, the control comprising means for tuning the controllable acoustic signal to characteristic frequencies of the fibers;

an acoustic signal sensor for measuring acoustic signals from the pulp fluid, wherein the acoustic signal sensor is arranged to measure at least one spectral component resulting from the interaction of the controllable acoustic signal and the fibers, the at least one spectral component including at least one property selected from the list of amplitude, phase, and time-delay; and a data processor connected to the acoustic signal sensor and operative to predict mechanical/chemical properties of fibers in the pulp fluid based upon the measured acoustic signals.

33. An apparatus for analysis of a pulp fluid comprising:

an acoustic signal source arranged to emit a controllable acoustic signal into the pulp fluid for interaction with the fibers;

a control operative to control the acoustic signal source;

an acoustic signal sensor for measuring acoustic signals from the pulp fluid, wherein the acoustic signal sensor is arranged to measure at least one spectral component resulting from the interaction of the controllable acoustic signal and the fibers, the at least one spectral component including at least one property selected from the list of amplitude, phase, and time-delay; and a data processor connected to the acoustic signal sensor and operative to predict based upon the measured acoustic signals mechanical/chemical properties of fibers in the pulp fluid and properties of paper manufactured by the pulp.

* * * * *